United States Patent [19]

Krause

[11] Patent Number: 4,506,224

[45] Date of Patent: Mar. 19, 1985

[54] HIGH-FREQUENCY FIELD SYSTEM FOR NUCLEAR MAGNETIC RESONANCE APPARATUS

[75] Inventor: Norbert Krause, Heroldsbach, Fed. Rep. of Germany

[73] Assignee: Siemens Aktiengesellschaft, Munich, Fed. Rep. of Germany

[21] Appl. No.: 405,727

[22] Filed: Aug. 6, 1982

[30] Foreign Application Priority Data

Aug. 24, 1981 [DE] Fed. Rep. of Germany ....... 3133432

[51] Int. Cl.$^3$ ............................................ G01R 33/08
[52] U.S. Cl. ..................................... 324/319; 324/300
[58] Field of Search ......................... 324/300, 318, 319

[56] References Cited

U.S. PATENT DOCUMENTS

| 3,461,350 | 8/1969 | Rioux | 324/319 |
|---|---|---|---|
| 4,310,799 | 1/1982 | Hutchison | 324/319 |
| 4,339,718 | 7/1982 | Ball | 324/319 |
| 4,362,993 | 12/1982 | Young | 324/319 |

FOREIGN PATENT DOCUMENTS

| 21535A1 | 1/1981 | European Pat. Off. . |
| 2840178 | 3/1980 | Fed. Rep. of Germany . |

Primary Examiner—Michael J. Tokar
Attorney, Agent, or Firm—Kenyon & Kenyon

[57] ABSTRACT

An apparatus for generating a substantially homogeneous magnetic high-frequency field and/or for receiving high-frequency signals in a nuclear magnetic resonance apparatus, such as zeugmatography. The apparatus contains at least two conductor sections of predetermined length which extend on a least one imaginary cylindrical surface parallel to the axial direction of the cylindrical surface. The conductor sections are adapted to carry current in opposite directions when connected to either external feeding or external receiving devices. In one embodiment, the arrangement operates at frequencies of illustratively 20 MHz so as to provide an improved signal-to-noise ratio over prior art systems. An envelope formed of electrically conductive material is adapted to be impervious to high-frequency energy, but permeable to low-frequency energy, and further adapted to be concentrically arranged with respect to the imaginary cylindrical surface about the conductor sections. The ends of the conductor sections which are arranged distal to the energy or receiving devices are terminated by means which reflect waves of high-frequency energy to produce in-phase high-frequency fields.

13 Claims, 4 Drawing Figures

HIGH-FREQUENCY FIELD SYSTEM FOR NUCLEAR MAGNETIC RESONANCE APPARATUS

BACKGROUND OF THE INVENTION

This invention relates generally to systems for generating high-frequency fields, and more particularly, to a system for generating a substantially homogeneous, high-frequency magnetic field for use in a nuclear magnetic resonance apparatus.

In nuclear magnetic resonance systems, particularly for nuclear spin resonance tomography or zeugmatography, high-frequency magnet systems are used for producing high-frequency magnetic fields and for receiving high-frequency signals. A known arrangement for practicing zeugmatography is provided with at least two conductor sections of predetermined length which extend along at least one imaginary cylindrical surface in a direction parallel to a cylindrical axis. Current flows through the two conductor sections in opposite directions; the conductor sections being connected to at least one external power supply or signal receiver, respectively. A system of this type is described in European patent application EP 21 535 A1.

In the field of medical diagnostics, imaging methods have been proposed in which an image which is similar to an X-ray tomogram is constructed by the computed or measured analysis of integrated proton resonsance signals from the spatial spin density and/or relaxation time distribution of a body to be examined. This method, which is also called "zeugmatography", is described in the publication "Nature", volume 242, 1973, pages 190–191.

During the application of nuclear spin resonance, the body to be examined, which may be a human body, is placed in a strong homogeneous magnetic field. The magnetic field, which is also called the base field, is superimposed by constant and/or pulsed gradient fields. Moreover, a high-frequency field which is oriented perpendicularly in the base field, must be developed which is also as homogeneous as possible. The physical dimensions of the system must be matched to the dimensions of the body to be examined so that the body can be placed, without difficulty, into the conductor system which generates the magnetic fields.

It is well known that in the apparatus of nuclear spin tomography or zeugmatography, the quality of sectional images which are produced depends upon the signal-to-noise ratio of the induced nuclear spin resonance signal. Since the signal-to-noise ratio depends upon the magnetic base field and its frequency, it is desirable to provide frequencies as high as possible in the base fields. See, for example, "J. Phys. E. Sci. Instrum.", volume 13, 1980, pages 38–44.

In the known nuclear magnetic resonance systems, only relatively low frequencies of approximately 5 MHz can be provided as a result of physical limitations. The high-frequency magnet fields are produced by coils which have the shape of a saddle. Such coils, which are arranged on at least one imaginary cylindrical surface, have straight conductor sections which extend parallel to the direction of the axis of the cylinder, and are provided at the end faces with arc-shaped conductor sections which extend in the circumferential direction. In this manner, the current in the conductor section in one straight side of the coil flows in a direction which is opposite to the flow of current in the other straight side. The axial length of the straight conductor sections and therefore, of the coils, is predetermined by the dimensions of the body to be examined. The entire wire length of the coil may be, for example, on the order of several meters. In coils of such dimensions, however, phase shifts of the fields between the beginning and end of the conductor of the coils occurs at the desired higher frequencies, above 5 MHz. This occurs because the lengths of the conductor are in the order of magnitude of the wavelength of the high frequency. As a result of these phase shifts, the quality of the fields which are generated by the coils decreases with increasing frequency. Moreover, undesirable coupling occurs with metallic parts of the component which surround the high frequency coils, such as the gradient coils or the base field magnet. This produces additional disturbances and eddy currents which attenuate the high-frequency field in the interior of the body to be examined. Moreover, the known "skin effect" renders the field in the body to be examined inhomogenenous. It is, therefore, not directly possible to increase the frequencies of operation and thereby improve the signal-to-noise ratio of the known nuclear magnetic resonance equipment.

It is, therefore, an object of this invention to provide a nuclear magnetic resonance apparatus having an arrangement for generating an essentially homogeneous magnetic high-frequency field in such a manner that a relatively large signal-to-nosie ratio is achieved which would correspond to an operating frequency of illustratively 20 MHz.

SUMMARY OF THE INVENTION

The foregoing and other objects are achieved by this invention which provides an envelope which is largely impermeable to high frequencies, but is permeable to low frequencies. The envelope is provided with an electrically highly conductive material arranged at a predetermined distance concentrically on an imaginary cylindrical surface around the conductor sections. Moreover, the envelope is connected to an apparatus for supplying or receiving energy. The conductor sections are arranged to form at least one conductor pair which is connected at its end which is not connected to the energy supplying or receiving apparatus so as to reflect the waves of the high-frequency field. In this manner, a conductor system which is formed by the envelope and at least one conductor pair develops a high-frequency field which oscillates in phase.

It is a particularly advantageous aspect of this invention that the propagation of a wave having a very high frequency is possible between the conductor pair and the envelope thereby creating resonance conditions where fields which are in phase are generated in the entire volume of interest. In other words, standing waves are developed on the conductor pair. The length of the conductor sections which would otherwise be required for the resonance of high frequencies, such as 20 MHz, are advantageously reduced to a size which is adapted to the body to be examined by circuitry at the end of the conductor sections facing away from the energy supply side. In this manner, very high frequencies can be provided, and the signal-to-noise ratio is correspondingly improved.

Since the common envelope around the conductor pair is formed so as to be substantially impervious to high frequency, but permeable to low frequency, coupling effects with components outside of the envelope can be substantially eliminated. The envelope therefore represents, in addition to a conducting body, a high-frequency shield for the high-frequency field against these components. As a result of the low frequency permeability of the envelope, however, the low frequency gradient fields can propagate largely unimpeded in the volume into which the body to be examined is to be placed.

BRIEF DESCRIPTION OF THE DRAWINGS

Comprehension of the invention is facilitated by reading the following detailed description in conjunction with the annexed drawings, in which.

DETAILED DESCRIPTION

Nuclear magnetic resonance apparatus, illustratively for zeugmatography, for which the high-frequency field system of the present invention is to be provided is based upon known nuclear magnetic resonance equipment, such as is described in European patent application 21 531 A1 or in DE OS 28 40 178. Generally, such equipment contains at least one normal or superconducting field coil system which is arranged concentrically around the z-axis of an orthogonal x, y, z coordinate system. The field coil generates a strong base field which is as homogeneous as possible in the z-direction. In addition, gradient coils are provided for generating sufficiently constant magnetic field gradients. The magnet coils permit axial accessibility to the homogeneous field region in its center. Usually, a human body to be examined is placed in the magnetic field along the z-axis. Nuclear spin is excited by means of a high-frequency field which is directed perpendicularly to the z-axis.

Figure 1:
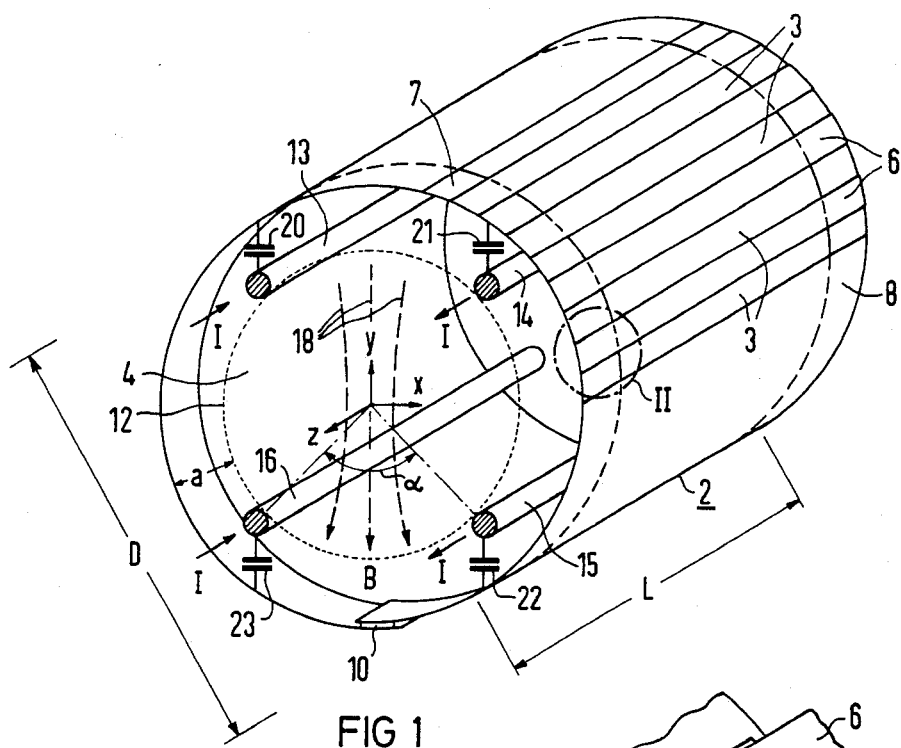
FIG. 1 is a schematic, isometric view of a high-frequency field arrangement constructed in accordance with the principles of the invention.

FIG. 1 shows an isometric, schematic view of a high-frequency field arrangement which is constructed in accordance with the principles of the invention and is suitable for the above-stated purpose. The high-frequency field arrangement is provided with a cage-like hollow, cylindrical envelope 2 having an axis which is oriented in the direction of the z-coordinate of an orthogonal x, y, z coordinate system. The envelope has an axial length L and a diameter D, and may consist of an electrically highly conductive material such as copper which may be plated with silver on at least one side. Moreover, as shown in the figure, the envelope need not be completely closed, but may be provided with openings, such as openings 3. Such openings facilitate penetration of low frequency magnetic fields, illustratively a gradient field, into the interior 4 and closed thereby. The envelope is thus designed to essentially prevent the development of low frequency current loops.

Figure 2:
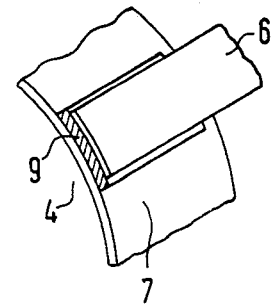
FIG. 2 is an isometric, expanded view of the area labelled II in FIG. 1.

In accordance with the illustrative embodiment of the invention in FIG. 1, envelope 2 is provided with ribbon-shaped longitudinal bars 6 which are oriented in the z-direction, and are spaced from one another. In addition, longitudinal bars 6 are connected at both ends of the hollow cylinder by rings 7 and 8. This mechanical affixation, however, is made by metallic contact on only one side; the connection being capacitive on the other side. As can be seen from the detail of FIG. 1 which is shown in FIG. 2, the longitudinal bars 6 overlap ring 7, and an insulating foil 9 is respectively arranged between the ring and the bars. In this manner, capacity is provided in the overlap zone. The magnitude of the capacitance is selected to provide low high-frequency impedance, but high low-frequency impedance.

In order to prevent low frequency circulating currents in rings 7 and 8, but to ensure a high-frequency short circuit, the rings are interrupted by a capacity in a suitable manner. In FIG. 1, the capacitance is formed in an overlap region by a foil 10 which is visible only for ring 7.

As an alternative to the embodiment of FIG. 1 which consists of envelope 2 formed of rings 7 and 8 and bars 6 which consist of solid electrically conductive material, an envelope of insulating material may be provided which carries on at least one of its surfaces a layer of an electrically conductive material, such as silver. The thickness of the layer must be at least as deep as the depth of penetration of the high-frequency current. In order to ensure that the layer is impervious to high frequency and permeable to low frequency, the layer may be optionally structured so as to have capacitive interruptions.

Envelope 2 encloses electric conductors which are arranged on at least one imaginary cylindrical surface 12. A radial distance a is arranged between envelope 2 and imaginary cylindrical surface 12 which is arranged concentrically within the envelope, and is indicated in the figure by a dotted line. At least two conductor sections which form a conductor pair are provided, the conductor sections being adapted to conduct current in opposite directions. In order to generate fields as homogeneous as possible in the interior of the envelope, at least four conductor sections of two conductor pairs are provided. A first conductor pair is formed of conductors 13 and 14 through which current flows in opposite directions. Conductor sections 15 and 16 represent the other conductor pair. The conductor sections of each conductor pair are arranged on imaginary cylindrical surface 12 in such a manner that they enclose, along a x-y plane, an angle of arc α which is between 45° and 150°, and preferably about 120°, along the circumferential direction of the cylinder.

In this arrangement, a high-frequency magnetic field B is generated, in accordance with the invention, which is indicated by broken lines 18 having arrows; the field being substantially homogeneous at least in the vicinity of the axis of the cylinder, and being perpendicular to the z-axis. Magnetic field B is produced by a high-frequency current which is conducted from an energy supply device (not shown) into the conductor sections 13 to 16 and envelope 2. The high-frequency current is provided in such a manner that standing waves are developed in the conductor sections and the envelope, while the system is operated at resonance. As indicated by the undesignated current arrows which are shown axially with the conductor sections, the current I flows in diametrically opposed conductor sections in opposite directions. Thus, in-phase high-frequency fields are generated in the entire volume of interest.

In the design of the inventive system, the distance between the conductor sections and the envelope depends on the frequency to be transmitted and the current, and therefore must not be chosen too large. In one embodiment, a distance a between imaginary cylindrical surface 12 and envelope 2 is at most 20 cm, and preferably at most 10 cm. A sufficient high-frequency coupling of these parts must be assured. The smallest value of distance a should not be less than 0.5 cm, and preferably not less than 1 cm.

For high frequencies of illustratively 20 MHz, conductor sections having a length L of, for example, 7.5 m would be required for resonance operation. By means of circuitry provided at the beginning or end of the system of conductor sections 13 to 16, and envelope 2, the length required for resonance operation can be reduced to the desired dimension. Persons of skill in the art can produce such terminating circuitry. Capacitors having predetermined values must be provided at the ends of conductor sections 13 to 16. In accordance with the embodiment of FIG. 1, a plurality of capacitors 20 to 23 are connected as lumped capacitances between the ends of the conductor sections and envelope 2. The value C of these capacitances is approximated by the formula $$C \simeq \left[\left|\omega Z_L \tan\left(\frac{\pi L}{\lambda}\right)\right|\right]^{-1}$$

where $\omega = 2\pi f$ is the angular frequency, $Z_L$ is the wave impedance of a conductor section against the envelope, and $\lambda$ is the wavelength.

In order to assure the required resonance operation, matching of the energy feeding device must be provided in addition to matching the capacitors. Advantageously, the match is selected so that the current nodes of the currents which are fed into the conductor system of envelope 2 and conductor sections 13 to 16 lie at least approximately in the axial center. In other words, the nodes should lie at the length L/2 of the envelope or conductor sections. In addition to the embodiment of FIG. 1 where the capacitances are provided by capacitors 20 to 23, short-circuited conductor sections can be provided for generating the capacitances.

It is not absolutely necessary to provide a feed system from only one side, as was assumed in the embodiment of FIG. 1, to produce a linearly polarized magnetic field B. Conductors 13 and 16 at one end face, and conductors 14 and 15 at the other end face can be connected to at least one external energy feeding device. The capacitances must then be provided on the respectively opposite sides of the conductor sections.

In a particularly advantageous embodiment of the invention, a circularly polarized magnetic field can be generated with the high-frequency device, according to the invention. Such a field has a better penetration behavior into the body to be examined than a linearly polarized high-frequency field because the field strength drop at high frequencies, illustratively above 20 MHz, is substantially smaller for a circularly polarized field than for a directional linearly polarized field. This means that high frequencies in this order of magnitude can be provided so that the signal-to-noise ratio is correspondingly improved. A further corresponding system of conductor sections is required to produce such a circularly polarized magnetic field instead of a single system of conductor sections as would be required to generate a linearly polarized magnetic field. This second conductor system must be arranged so as to be rotated in the circumferential direction with respect to the axis of the cylinder relative to the first conductor system, where the high-frequency currents in the conductor sections of this second conductor system are shifted in-phase by a predetermined phase angle with respect to the high-frequency currents in the first conductor system. In a two conductor system, such a phase shift is 90°. The amplitudes of the high-frequency currents, however, should be approximately equal. A high-frequency field device for generating a circularly polarized magetic field is described in German patent application P 31 31 946.7.

In order that an in-phase, high-frequency field be developed in resonance with the conductor system of envelope 2 and conductor sections 13 to 16 in FIG. 1, four generators are required as the energy feeding device if each conductor sections is to be excited individually. This number of generators can be reduced to two by connecting conductor sections of the same current flow direction, i.e., the conductor sections 13 and 16, and conductor sections 14 and 15, in parallel. If the conductor sections are connected in parallel, it is further possible to provide only one generator instead of two generators if the current fed into the one parallel-connected conductor sections are phase shifted relative to the current in the other parallel-connected conductor sections by λ/2. A special phase shifter or cable section having a length λ/2 can be used for this purpose. Such phase sections can be dispensed with if the current is fed in from two opposite sides.

In addition to feeding the current to conductor sections 13 to 16 as shown in FIG. 1, other types of excitation are possible. Such other types of excitation include the use of a larger number of conductor sections. Thus, conductor sections 13 to 16 can also be excited in pairs by connecting the conductor sections 13 and 16 as well as the conductor sections 14 and 15 in parallel. The conductor system so produced can be considered as a system with two conductor units through which current flows in opposite directions, each unit having two conductor sections. Conductor systems with several such conductor units are also possible wherein each conductor unit can comprise a larger number of conductor sections. Such a system is schematically indicated in cross-section in FIG. 3.

Figure 3:
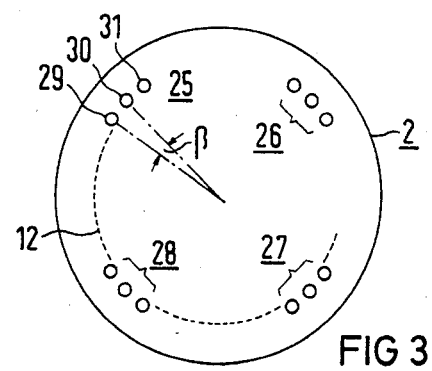

FIG. 3 shows a system of conductors arranged in an envelope 2 and which comprises four conductor units 25 to 28. Each of the conductor units has three parallel conductor sections 29 to 31, each with circular cross-section. The conductor sections are arranged on the outer cylindrical surface of at least one imaginary cylinder 12 which is arranged concentrically within envelope 2. In this embodiment, the angle of arc β between adjacent conductor sections is advantageously selected to be between 5° to 30°, and preferably between 20° to 25°. In this manner, the homogeneity of the high-frequency magnetic field is further improved.

Figure 4:
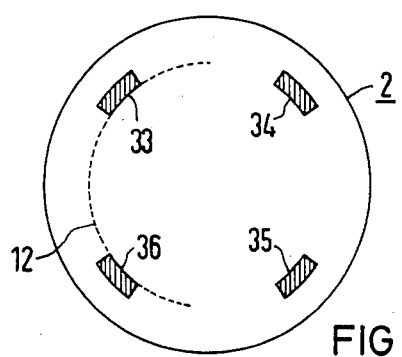
FIGS. 3 and 4 show different embodiments of conductor sections for the high-frequency field apparatus.

FIG. 4 shows a high-frequency field arrangement similar to that of FIG. 3. However, contrary to the embodiment of FIG. 3, the embodiment of FIG. 4 is provided with conductor units 33 to 36 which are each formed of a single ribbon-shaped conductor section which is bent so as to correspond to the curvature of cylindrical surface 12. In this manner, the conductor sections 29 to 31 of FIG. 3 are combined in the embodiment of FIG. 4 to produce a single ribbon-shaped conductor section.

In the embodiments of the foregoing figures, it was assumed that the conductor sections and the envelope are connected to at least one external energy supply device. Since the high-frequency field device according to the invention may also be used for receiving high-frequency signals, the conductor sections and the envelope must be connected, in this case, to a suitable external receiver system.

Although the invention has been described in terms of specific embodiments and applications, persons skilled in the art, in light of this teaching, can generate additional embodiments without exceeding the scope or departing from the spirit of the claimed invention. Accordingly, it is to be understood that the drawings and descriptions in this disclosure are proffered to facilitate comprehension of the invention and should not be construed to limit the scope thereof.

What is claimed is:

1. An apparatus for selectably generating a substantially homogeneous magnetic high-frequency field and receiving high-frequency signals in a nuclear magnetic resonance system, the apparatus having a plurality of conductor sections of predetermined length having first and second ends and spaced apart from a central axis and arranged parallel thereto, the conductor sections being each selectably coupled at one of said ends thereof to one of a source of alternating high-frequency electric current and a receiver of alternating high-frequency electric current generated by a high-frequency voltage induced in said conductor sections and being arranged in at least one first pair so as to conduct alternating high-frequency electric current in opposite directions in each of the two conductors of said pair, the apparatus further comprising:

envelope means comprising electrically conductive material arranged so that said envelope means is impervious to high-frequency energy and permeable to low frequency energy, said envelope means being arranged concentrically with said central axis and at a predetermined distance from said conductor sections and about the conductor sections, said envelope means being selectably electrically coupled to said source of alternative high-frequency electric current and said receiver of alternating high-frequency electric current; and termination means coupled to the other of said ends of said conductor sections, said termination means electrically terminating said conductor sections and said envelope means so as to generate standing waves of said alternating high-frequency current in said conductor sections and said envelope means by reflecting said waves whereby an in-phase high-frequency magnetic field is developed by a conductor system formed by said envelope means and said at least one first pair of conductor sections.

2. The apparatus of claim 1 wherein said source and receiver are resonantly matched to said conductor sections and said envelope means.

3. The apparatus of claim 2 wherein said termination means and said match of said source and receiver to said conductor sections and said envelope means are selected so as to produce current nodes in said envelope means and said conductor sections, said current nodes being disposed approximately at the axial center of said envelope means and said conductor sections.

4. The apparatus of claim 1 wherein said electrically conductive material is arranged in the form of a cage provided with openings between portions of said electrically conductive material.

5. The apparatus of claim 1 wherein said termination means comprises a capacitance having a predetermined value.

6. The apparatus of claim 5 wherein said capacitance comprises a short-circuited conductor section connected between at least one of the conductor sections and said envelope means.

7. The apparatus of claim 5 or 6 wherein said predetermined capacitance value is determined approximately in accordance with the formula $$C \simeq \left[ \omega Z_L \tan\left(\frac{\pi L}{\lambda}\right) \right]^{-1},$$

where $\omega$ is the angular frequency, $Z_L$ is the wave impedance of a conductor section against said envelope means, L is an axial dimension of a selectable one of said envelope means and the conductor sections, and $\lambda$ is a wavelength of said alternating high-frequency electric current.

8. The apparatus of claim 1 wherein a plurality of conductor sections are combined to form a conductor unit, a system for generating the magnetic high-frequency field being formed by at least a pair of said conductor units and said envelope means, said alternating high-frequency electric current flowing in opposite directions in each of said conductor units in said pair of conductor units.

9. The apparatus of claim 1 or 8 wherein the conductor sections comprise at least one ribbon-shaped conductor strand.

10. The apparatus of claim 1 comprising at least two of the conductor pairs of the conductor sections.

11. The apparatus of claim 10 further comprising a second conductor section pair spaced apart from said central axis and arranged parallel thereto and at a predetermined distance from said envelope means inside said envelope means, said conductor section pair being rotated in the circumferential direction by a predetermined angle with respect to the first pair of conductor sections and conducting a high-frequency current which is shifted in-phase by a predetermined phase angle with respect to the high-frequency current in said first pair of conductor sections, the high-frequency electric currents in said first and second conductor section pairs having approximately equal amplitudes.

12. The apparatus of claim 10 wherein said first and second conductor section pairs are disposed at distance defined by first and second respective concentric circles separated by a predetermined radial distance.

13. The apparatus of claim 12 wherein a minimum distance between a selectable one of said first and second conentric circles and said envelope means is at least 0.5 cm and a maximum distance between said envelopes means and either of said first and second concentric circles is less than 20 cm.

* * * * *